United States Patent
Ichikawa et al.

(10) Patent No.: US 8,148,590 B2
(45) Date of Patent: Apr. 3, 2012

(54) PROCESS FOR PRODUCING AROMATIC HYDROCARBON AND HYDROGEN

(75) Inventors: Masaru Ichikawa, Sapporo (JP); Ryoichi Kojima, Sapporo (JP); Yuji Ogawa, Saitama (JP); Masamichi Kuramoto, Tokyo (JP)

(73) Assignees: Meidensha Corporation, Tokyo (JP); Masaru Ichikawa, Sapporo-shi (JP)

( * ) Notice: Subject to any disclaimer, the term of this patent is extended or adjusted under 35 U.S.C. 154(b) by 939 days.

(21) Appl. No.: 11/658,399

(22) PCT Filed: Jul. 28, 2005

(86) PCT No.: PCT/JP2005/013864
§ 371 (c)(1),
(2), (4) Date: Jan. 26, 2007

(87) PCT Pub. No.: WO2006/011568
PCT Pub. Date: Feb. 2, 2006

(65) Prior Publication Data
US 2008/0312483 A1 Dec. 18, 2008

(30) Foreign Application Priority Data
Jul. 28, 2004 (JP) .................................. 2004-219530

(51) Int. Cl.
*C07C 15/00* (2006.01)
(52) U.S. Cl. ........ 585/407; 585/417; 585/418; 585/419; 585/420; 585/943
(58) Field of Classification Search .................. 585/418, 585/419, 420, 943, 906
See application file for complete search history.

(56) References Cited

U.S. PATENT DOCUMENTS

| | | | |
|---|---|---|---|
| 6,552,243 | B2 | 4/2003 | Allison et al. |
| 2001/0008949 | A1 | 7/2001 | Wu et al. |

FOREIGN PATENT DOCUMENTS

| | | |
|---|---|---|
| JP | 10-272366 A | 10/1998 |
| JP | 11-047606 A | 2/1999 |

(Continued)

OTHER PUBLICATIONS

Qi et al, "Research progress of aromatization of methane", Modern Chemical Industry, 2002, 22(8): 13-17.

(Continued)

*Primary Examiner* — Tam M Nguyen
(74) *Attorney, Agent, or Firm* — Foley & Lardner LLP

(57) ABSTRACT

A process for producing aromatic hydrocarbons and hydrogen, in which a lower hydrocarbons-containing feedstock gas is reformed by being supplied to and being brought into contact with a catalyst under high temperature conditions thereby forming aromatic hydrocarbons and hydrogen. The method includes the steps of (a) supplying a hydrogen gas together with the feedstock gas during a supply of the feedstock gas; and (b) suspending the supply of the feedstock gas for a certain period of time while keeping a condition of a supply of the hydrogen gas. The catalyst is exemplified by a metallo-silicate carrying molybdenum and a metallo-silicate carrying molybdenum and rhodium. An amount of the hydrogen gas supplied together with the feedstock gas is set to be preferably larger than 2% and smaller than 10%, more preferably within a range of from 4 to 8%, much more preferably 8%. As a pretreatment for a reforming reaction by which aromatic hydrocarbons and hydrogen are formed, the catalyst is increased in temperature and kept at the temperature for a certain period of time while a gas containing methane and hydrogen is supplied thereto.

8 Claims, 5 Drawing Sheets

FOREIGN PATENT DOCUMENTS

| | | |
|---|---|---|
| JP | 11-60514 A | 3/1999 |
| JP | 2003-026613 A | 1/2003 |
| JP | 2004-621070 A | 7/2004 |
| JP | 2004-269398 A | 9/2004 |
| JP | 2005-255605 A | 9/2005 |
| WO | WO 02/10099 A2 | 2/2002 |

OTHER PUBLICATIONS

Office Action issued by Chinese Patent Office dated Aug. 21, 2009 for Chinese Patent Application No. 2005800253112.

L. Wang et al., "Selective Dehydroaromatization of Methane Toward Benzene on Re/HZSM-5 Catalysts and Effects of $CO/CO_2$ Addition," Journal of Catalysis, vol. 190, 2000, pp. 276-283.

R. Ohnishi et al., "Catalytic Dehydrocondensation of Methane with CO and $CO_2$ Toward Benzene and Naphthalene on Mo/HZSM-5 and Fe/Co-Modified Mo/HZSM-5," Journal of Catalysis, vol. 192, 1999, pp. 92-103.

H. Ma et al., "Highly Stable Performance of Methane Dehydroaromatization on Mo/HZSM-5 Catalyst with a Small Amount of $H_2$ Addition into Methane Feed," Catalysis Letters, vol. 89, Nos. 1-2, 2003, pp. 143-146.

K. Honda et al., "Methane Dehydroaromatization over Mo/HZSM-5 in Peridic $CH_4$-$H_2$ Switching Operation Mode," Catalysis Communication, vol. 4, 2003, pp. 21-26.

PROCESS FOR PRODUCING AROMATIC HYDROCARBON AND HYDROGEN

TECHNICAL FIELD

The present invention relates to an advanced use of natural gas, biogas and methane hydrate which contain methane as a main component, more particularly to a process for efficiently producing aromatic compounds and hydrogen of high purity from methane. A main component of aromatic compounds is exemplified by benzene and naphthalene which are materials of chemical products such as plastics.

BACKGROUND OF THE INVENTION

Aromatic hydrocarbons exemplified by benzene, toluene and xylene are conventionally formed from naphtha and coal tar mainly. Concerning the former, petroleum resource is applied as a raw material but low in yield of aromatic hydrocarbons. Concerning the latter, coal is applied as an inexpensive raw material, but it requires a large amount of organic solvent since a solvent extraction method is employed.

As a method for forming hydrogen gas, a steam reforming method for natural gas and naphtha is currently known. However, the steam reforming method requires a high temperature of about 900° C. Further, a large amount of raw material is burned in order to maintain the temperature for reforming, and additionally steam is used three to four times as large as a theoretical-required amount in order to prevent the catalytic activity reduction, thereby consuming an extremely large amount of energy. Additionally, the steam reforming method is burdened with a problem of generating such products upon reforming and burning as to cause global warming, i.e., a large amount of carbon dioxide.

On the other hand, as a process for producing aromatic hydrocarbons such as benzene and naphthalene and hydrogen from lower hydrocarbons, more particularly from methane, a so-called direct-conversion of methane is generally known. The direct conversion of methane is a method for decomposing methane directly on a catalyst in the absence of oxygen gas, in which rhenium carried on zeolite (HZSM-5) is regarded as an effective catalyst (as disclosed in non-patent documents 1 and 2). However, the direct conversion method is burdened with problems of an extreme decrease in catalytic activity due to deposited carbon and of a low conversion ratio of methane.

As one of methods for solving these problems, a method is proposed in patent document 1, in which a direct conversion of methane is carried out in the presence of carbon monoxide or carbon dioxide of a few percents; however, the carbon monoxide or carbon dioxide remains in the product gas so as to burden the purification and separation of a main product, more specifically hydrogen gas, which is not practical.

In order to solve this problem, the other method is proposed in patent document 2. In this method for producing aromatic hydrocarbons and hydrogen, lower hydrocarbons and a gas containing hydrogen or a hydrogen gas are cyclically and alternately brought into contact with a catalyst, thereby forming aromatic hydrocarbons and a high-purity hydrogen without inducing the catalytic activity decrease.

In the method for producing aromatic hydrocarbons and hydrogen, relating to patent document 2, a supply of lower hydrocarbons (such as methane gas) and a supply of hydrogen gas are alternately changed at the same flow rate and at short intervals, e.g., at every five minutes, as shown in FIG. 3 of the present invention (a schedule of supplying hydrogen and lower hydrocarbons, according to conventional techniques), thereby maintaining the effect of the catalyst (see paragraph 0020 of patent document 2). Specifically, it is required to alternately carry out the change of the supply of methane gas and the supply of hydrogen gas at short intervals. Additionally, the reaction is not made while the hydrogen gas flows, so that a substantial period of time for the reaction for forming aromatic hydrocarbons and hydrogen is half of an apparent period of time for forming them. Further, hydrogen gas is used as same amount as methane gas in this method, which is economically disadvantageous.

When the intervals between the alternations of the supply of methane and hydrogen are extended in the above method, e.g., when a the supply of methane is set to 80 minutes and that of hydrogen is set to 20 minutes (as disclosed in paragraph 0022 of patent document 2), producing rates of aromatic hydrocarbons and hydrogen are significantly decreased and additionally a producing fluctuation per hour is large, as compared with the method of the 5-minute interval. In this case, hydrogen gas is used as same amount as methane gas, more specifically a time ratio between methane and hydrogen is 4:1, much more specifically an amount of hydrogen corresponds to 20% by volume of an amount of methane. This method is recognized to have an effect of lasting the catalytic effect; however, aromatic hydrocarbons and hydrogen can not be formed efficiently.

Non-patent document 1: "JOURNAL OF CATALYSIS" 182, 92-103 (1999)

Non-patent document 2: "JOURNAL OF CATALYSIS" 190, 276-283 (2000)

Patent document 1: Japanese Patent Provisional Publication No. 11-60514

Patent document 2: Japanese Patent Provisional Publication No. 2003-26613

DISCLOSURE OF THE INVENTION

In view of the above, an object of the present invention is to provide a process for producing aromatic hydrocarbons and hydrogen, the process maintaining a catalytic activity continuously thereby allowing an efficient production of aromatic hydrocarbons and hydrogen.

A process for producing aromatic hydrocarbons and hydrogen, according to a first embodiment, is a process in which a lower hydrocarbons-containing feedstock gas is reformed by being supplied to and being brought into contact with a catalyst under high temperature conditions thereby forming aromatic hydrocarbons and hydrogen. The process is characterized by including the steps of (a) supplying a hydrogen gas together with the feedstock gas during a supply of the feedstock gas; and (b) suspending the supply of the feedstock gas for a certain period of time while keeping a condition of a supply of the hydrogen gas.

A process for producing aromatic hydrocarbons and hydrogen, according to a second embodiment, is based on the process for producing aromatic hydrocarbons and hydrogen, according to the first embodiment, and is characterized in that a pretreatment for a reforming reaction by which aromatic hydrocarbons and hydrogen are formed includes a step of increasing the catalyst in temperature and keeping the catalyst at the temperature for a certain period of time while supplying a methane gas thereto.

A process for producing aromatic hydrocarbons and hydrogen, according to a third embodiment, is based on the process for producing aromatic hydrocarbons and hydrogen, according to the first embodiment, and is characterized in that a pretreatment for a reforming reaction by which aromatic hydrocarbons and hydrogen are formed includes a step of increasing the catalyst in temperature and keeping the catalyst at the temperature for a certain period of time while supplying a gas containing methane and hydrogen thereto.

A process for producing aromatic hydrocarbons and hydrogen, according to a fourth embodiment, is based on the process for producing aromatic hydrocarbons and hydrogen, according to the third embodiment, and is characterized in that methane and hydrogen are supplied at a ratio of 1:4 during the pretreatment.

A process for producing aromatic hydrocarbons and hydrogen, according to a fifth embodiment, is based on the process for producing aromatic hydrocarbons and hydrogen, according to the third or fourth embodiment, and is characterized in that the pretreatment includes a step of keeping the catalyst at 700° C. for 6 hours while supplying the gas containing methane and hydrogen to the catalyst.

A process for producing aromatic hydrocarbons and hydrogen, according to a sixth embodiment, is based on the process for producing aromatic hydrocarbons and hydrogen, according to any of the first through fifth embodiments, and is characterized in that the catalyst includes metallo-silicate carrying molybdenum.

A process for producing aromatic hydrocarbons and hydrogen, according to a seventh embodiment, is based on the process for producing aromatic hydrocarbons and hydrogen, according to any of the first through fifth embodiments, and is characterized in that the catalyst includes metallo-silicate carrying molybdenum and rhodium.

A process for producing aromatic hydrocarbons and hydrogen, according to an eighth embodiment, is based on the process for producing aromatic hydrocarbons and hydrogen, according to any of the first through seventh embodiments, and is characterized in that an amount of the hydrogen gas supplied together with the feedstock gas is larger than 2% and smaller than 10% of the feedstock gas.

A process for producing aromatic hydrocarbons and hydrogen, according to a ninth embodiment, is based on the process for producing aromatic hydrocarbons and hydrogen, according to any of the first through eighth embodiments, and is characterized in that an amount of the hydrogen gas supplied together with the feedstock gas is within a range of from 4 to 8% of the feedstock gas.

A process for producing aromatic hydrocarbons and hydrogen, according to a tenth embodiment, is based on the process for producing aromatic hydrocarbons and hydrogen, according to the eighth or ninth embodiment, and is characterized in that an amount of the hydrogen gas supplied together with the feedstock gas is 8% of the feedstock gas.

According to the process for producing aromatic hydrocarbons and hydrogen of the first through ninth embodiments, the feedstock gas made of lower hydrocarbons is intermittently reacted with the catalyst while the hydrogen gas is continuously reacted with the catalyst. With this, the activity of the catalyst is regenerated during a period of time for supplying the hydrogen gas alone, so that aromatic hydrocarbons and hydrogen can be formed stably over a long period of time.

According to the process for producing aromatic hydrocarbons and hydrogen of the first through ninth embodiments, a gas containing methane gas or methane and hydrogen is supplied during the pretreatment for the reforming reaction, thereby suppressing a significant reduction in catalytic activity.

Examples of the catalyst include metallo-silicate carrying molybdenum, as discussed in the process for producing aromatic hydrocarbons and hydrogen according to the sixth embodiment. Particularly when metallo-silicate which carries rhodium (as the second metal) in addition to molybdenum is applied according to the process for producing aromatic hydrocarbons and hydrogen according to the seventh embodiment, aromatic hydrocarbons and hydrogen are formed while maintaining the efficiency of the regeneration of catalytic activity.

According to the process for producing aromatic hydrocarbons and hydrogen of the eighth through tenth embodiments, an amount of the hydrogen gas supplied together with the feedstock gas in the process for producing aromatic hydrocarbons and hydrogen is adjusted preferably to be larger than 2% and smaller than 10%, more preferably within a range of from 4 to 8%, much more preferably 8%. With this, the regeneration efficiency of catalytic activity is maintained thereby improving a period of time for lasting the catalytic efficiency. Further, aromatic hydrocarbons and hydrogen can be formed stably and inexpensively.

As discussed above, according to the process for producing aromatic hydrocarbons and hydrogen of the first through tenth embodiments relating to the present invention, the hydrogen gas is supplied together with the feedstock gas during the supply of the feedstock gas. With the thus added hydrogen gas, the catalytic activity is maintained over a long period of time. Even when the catalytic activity tends to be decreased due to generation of coke, the catalytic activity is recovered with hydrogen gas alone by cutting off the feedstock gas for a certain period of time. Therefore, aromatic hydrocarbons and hydrogen can be efficiently formed with such a simple operation as to supply or to cut off the feedstock gas, while maintaining the catalytic effect continuously.

DETAILED DESCRIPTION OF THE INVENTION

Figure 1:
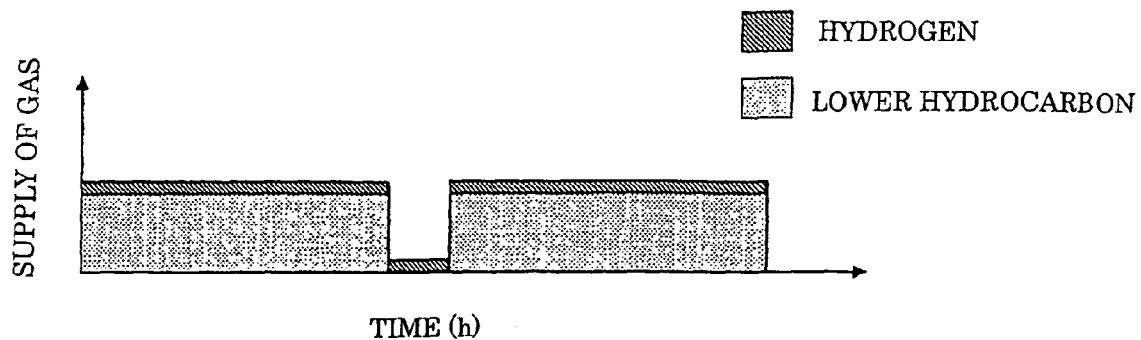
FIG. 1 is a schedule of supplying hydrogen and lower hydrocarbons, according to the present invention.

Referring now to the drawings, an embodiment according to the present invention will be discussed.

FIG. 1 shows a schedule of supplying hydrogen and lower hydrocarbons in a process for producing aromatic hydrocarbons and hydrogen, according to the present invention.

The present invention relates to a process for producing aromatic hydrocarbons and hydrogen, in which a lower hydrocarbons-containing feedstock gas is reformed by being supplied to and being brought into contact with a catalyst under high temperature conditions thereby forming aromatic hydrocarbons and hydrogen. The method includes the steps of (a) supplying a hydrogen gas together with the feedstock gas during a supply of the feedstock gas; and (b) suspending the supply of the feedstock gas for a certain period of time while keeping a condition of a supply of the hydrogen gas.

Examples of lower hydrocarbons contained in the feedstock gas include methane, ethane, ethylene, propane, propylene, n-butane, isobutane, n-butene, isobutene and the like.

As the above-mentioned catalyst, any known one can be employed as far as the feedstock gas brought into contact therewith forms aromatic hydrocarbons and hydrogen, and is exemplified by metallo-silicate carrying molybdenum (as disclosed in Japanese Patent Provisional Publications Nos. 10-272366 and 11.47606), and metallo-silicate carrying molybdenum and rhodium.

Examples of metallo-silicate carrying molybdenum and rhodium include aluminosilicate. Aluminosilicate is a porous material formed of silica and alumina and formed with pores of 4.5 to 6.5 angstrom in diameter, and is exemplified by molecular sieve 5β, faujasite (of type NaY or NaX), ZSM-5, HZSM-5, MCM-22. Additionally, the catalyst is exemplified by: porous materials (such as ALPO-5 and VPI-5) formed with micropores of 6 to 13 angstrom in diameter and containing phosphoric acid as a main component; a zeolite substrate formed with a channels; and porous substrates of mesopore type, such as FSM-16 and MCM-41, which contains silica as a main component and alumina as a part and is formed with cylindrical mesopores (or channel) of 10 to 1000 angstrom in diameter. Further, metallo-silicate is exemplified by metallo-silicate made of silica and titania, in addition to the above-mentioned aluminosilicate.

Examples according to the present invention will be described. It will be understood that these Examples are not to be construed to limit the scope of the invention.

(Basic Experiment)
1. Formation of Catalyst
(1) Carrying Molybdenum on Substrate A catalyst relating to this Example is produced in such a manner that zeolite (ZSM-5) which belongs to metallo-silicate carries molybdenum. Hereinafter, the procedure by which molybdenum is carried will be discussed.

First of all, 1300 g of hexaammonium heptamolybdate tetrahydrate (containing 750 g of molybdenum) was dissolved in 5 liters of distilled water, thereby preparing an impregnation solution. Subsequently, while the thus prepared impregnation solution was stirred by a high-speed agitator, 5 kg of the zeolite was added to the impregnation solution and then stirred for 3 hours. Further, the stirred substance was dried, i.e., so evaporated as to solidify, at 70 to 100° C. Thereafter, the dried substance was calcined in air at 550° C. for 5 hours, thereby obtaining zeolite powder which carries molybdenum at 15% by weight of the zeolite.

(2) Preparation of Components of the Catalyst

An inorganic component was so prepared as to be constituted of molybdenum-carrying zeolite (82.5 wt. %); clay (10.5 wt. %); and glass fiber (7 wt. %).

The catalyst was as a whole so prepared as to be constituted of the above-mentioned inorganic component (65.4 wt. %); an organic binder (13.6 wt. %); polymeric beads (which was available from Matsumoto Yushi-Seiyaku Co., Ltd. under the trade name of F-80E, and had an average diameter of 90 to 110 μm and a true specific gravity of 0.0025) (5.0 wt. %); and a water content (21 wt. %).

(3) Shaping the Catalyst

The inorganic component, the organic binder, polymeric beads and the water content were prepared in the above-mentioned preparation ratio, and then mixed or kneaded by a means of kneading (a kneader). Subsequently, the thus mixed substance was shaped by a vacuum extrusion machine into a rod (5 mm in diameter and 10 mm in length). An extrusion pressure applied during this shaping process was set within a range of from 70 to 100 kg/cm$^2$.

(4) Drying and Calcining the Catalyst

In order to eliminate the water content added in the shaping process, a drying process was carried out at 100° C. for about 5 hours.

Temperature-increasing rate and temperature-decreasing rate in a calcining process are set within a range of from 30 to 50° C./hour. During the calcining process, the temperature was kept within a range of from 120 to 150° C. for 2 hours in order not to instantaneously calcine the polymeric beads added in the shaping process. Thereafter, such a process that the temperature was kept within a range of from 250 to 450° C. for 2 to 5 hours in order not to instantaneously calcine the organic binder was carried out twice, thereby removing the binder. This is based on a reason that the binder calcines instantaneously so as to decrease the strength of the calcined substance when the temperature-increasing rate and the temperature-decreasing rate exceed the above-mentioned rate and when a temperature-keeping time is not ensured. By carrying out the processes as discussed above, a catalyst in the form of foam and carrying molybdenum in an amount of 15% was obtained. The properties of the catalyst are shown in Table 1.

TABLE 1

| Total volume of pores | Porosity | Diameter of pore located in the center | Specific surface measured by BET adsorption isotherm |
|---|---|---|---|
| 0.47 cm$^3$/g | 52% | 1.15 μm | 209 m$^2$/g |

2. Formation of Aromatic Hydrocarbons and Hydrogen 14 g of the catalyst was charged into a reaction pipe of a fixed bed flow type reactor (the pipe has an internal diameter of 18 mm and is produced in such a manner as to make a calorizing treatment on Inconel 800H's portion with which gas is brought into contact), and then subjected to a treatment for combining molybdenum with carbon under the following Pretreatment Conditions. Subsequently, a feedstock gas (lower hydrocarbons) and hydrogen were supplied to the reaction pipe under the following Reaction Conditions, thereby forming aromatic hydrocarbons and hydrogen. In this Example, methane was supplied as the lower hydrocarbons. Incidentally, argon gas added according to the following conditions is a dilution gas for conforming to a detection standard concentration of a gas detector by an internal standard method, and therefore does not contribute to the reaction. Additionally, two gas chromatographs were used in this experiment: one is available from Shimadzu Corporation under the trade name of GC-14B, and the other is available from Yokogawa Electric Corporation under the trade name of G2890A.

(Pretreatment Conditions) The catalyst was increased in temperature to 550° C. in air and then kept at the temperature for 1 hour. Thereafter, the catalyst was increased in temperature to 650° C. while a gas (CH$_4$+9Ar) which contains methane and argon was supplied thereto, and then kept at the temperature for 1 hour.

(Reaction Conditions)

Reaction temperature: 750° C.,

Reaction pressure: 0.2 MPaG,

Reaction gas: 100 parts of methane+10 parts of argon+7 parts of hydrogen (methane supplied at a space velocity of 3000 ml/h/g+argon supplied at a space velocity of 300 ml/h/g+hydrogen supplied at a space velocity of 210 ml/h/g).

Then, an operation of supplying hydrogen gas alone to the reaction pipe during formation of aromatic hydrocarbons and hydrogen was carried out. Specifically, formation of aromatic hydrocarbons and hydrogen was carried out by a reaction made for 17 hours under the above reaction conditions (which reaction was named as the first reaction). Thereafter, a valve for supplying methane gas and argon gas was closed so that hydrogen gas alone was supplied for 4 hours without any variation in the temperature and pressure (namely, at 750° C. and 0.2 MPaG), thereby regenerating the catalytic activity. Subsequently, the valve for supplying methane gas and argon gas was opened, thereby carrying out the formation of aromatic hydrocarbons and hydrogen under the above reaction conditions again (which formation was named as the second reaction).

Figure 2:
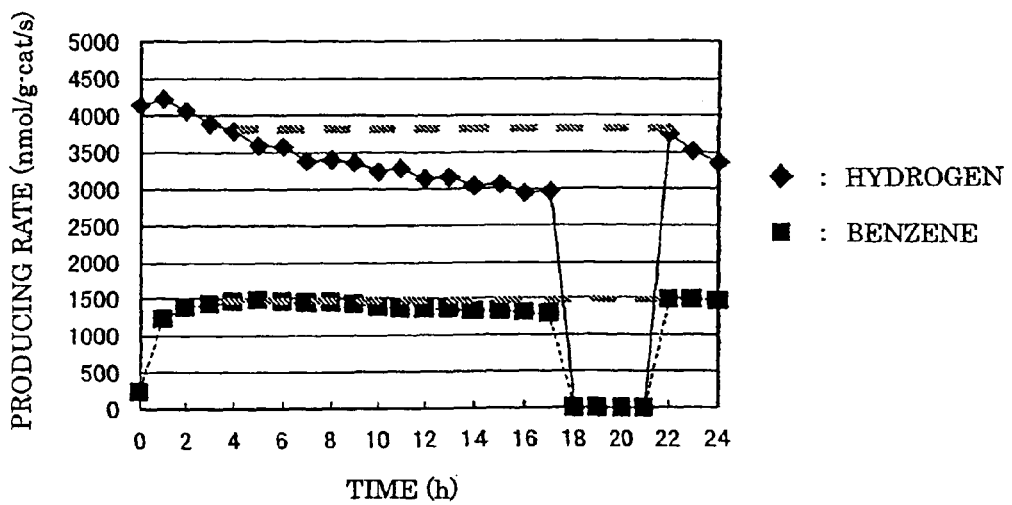
FIG. 2 is a characteristic graph showing a variation with time in each of a hydrogen-producing rate and benzene-producing rate.
Figure 3:
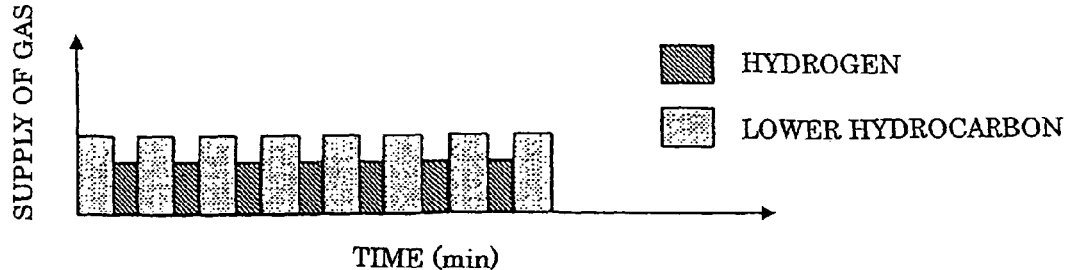
FIG. 3 is a schedule of supplying hydrogen and lower hydrocarbons, according to conventional techniques.

FIG. 2 is a characteristic graph showing a variation with time in each of a hydrogen-producing rate and benzene-producing rate. The hydrogen-producing rate is defined by "the number of nmol of hydrogen formed by 1 g of the catalyst per second". The benzene-producing rate is defined by "the number of nmol of benzene formed by 1 g of the catalyst per a second". Incidentally, black rhombuses represent a plot of hydrogen. Black squares represent a plot of benzene.

As apparent from the characteristic graph of FIG. 2, the benzene-producing rate during the first reaction is equal to that during the second reaction. With this, it is confirmed that a catalytic performance is recovered to an equal level to an initial stage.

Additionally, it is also confirmed that the supplying operation can be changed at a long time interval as follows:

a period of time over which the feedstock gas (methane gas) and hydrogen gas were supplied:a period of time over which hydrogen gas alone was supplied=17 hours (or 1020 minutes): 4 hours (or 240 minutes).

As a method for the above operation, a required thing during changing the supply of gas is only to close the valve of the feedstock gas (methane gas) thereby suspending the supply of feedstock gas.

Further, the characteristic graph of FIG. 2 shows that a period of time for supplying hydrogen gas is 21 hours while a period of time for supplying methane gas is 17 hours in this Example. However, hydrogen gas is supplied at a rate expressed as follows:

a space velocity of methane gas:a space velocity of hydrogen gas=100:7, so that the amount of the supplied hydrogen gas is 8.6% by volume of the supplied methane gas. Hence, this method is found to be economical as compared with conventional methods.

Based on the above results, the following facts were confirmed. When hydrogen gas is supplied together with the feedstock gas during the supply of feedstock gas, the catalytic activity is maintained for a long period of time with the added hydrogen gas. Even if the catalytic activity tends to be degraded due to generation of coke, the catalytic activity is recovered with hydrogen gas alone by cutting off the feedstock gas for a certain period of time. Aromatic hydrocarbons and hydrogen can be efficiently formed with such a simple operation as to supply or to cut off the feedstock gas while the catalytic effect is maintained continuously.

(Applied Experiment)

Concerning a formation of aromatic hydrocarbons and hydrogen of this reaction type, for example, Japanese Patent Provisional Publication No. 2004-269398 discloses that: mixing hydrogen with a feedstock gas inhibits a reaction for forming carbon and provides an effect of removing the carbon (formed in the above reaction) upon reducing the carbon to hydrocarbon, thereby inhibiting a catalytic degradation with time; and that the mixed hydrogen inhibits the reaction for forming aromatic hydrocarbons but improves a reaction-efficiency as a whole with its effect of suppressing the catalytic degradation.

The above patent publication discloses that an additive amount of hydrogen is within a range of from 1 to 20% by volume in a case of addition of hydrogen. The above range is preferable, which is based on the reasons that: an additive amount of hydrogen of less than 1% by volume does not provide a sufficient effect of suppressing a coating-formation on the surface of the catalyst due to the formed carbon, the coating-formation causing degradation of the catalytic activity, so that degradation of the catalytic performance cannot be sufficiently suppressed; and that an additive amount of hydrogen of more than 20% by volume increases an effect of preventing the aimed progress of catalytic reaction, so as not to provide a sufficient reaction-efficiency. It is further preferable that an upper limit is 5% by volume and a lower limit is 15% by volume.

Further, a concrete experiment was disclosed (as Example 2) in such a manner as to use a catalyst which carries molybdenum at 6% by weight and named as 6 wt. %-Mo/HZSM-5. A mixture gas is prepared by adding hydrogen to methane at 6% by volume. In the use of the mixture gas as a feedstock gas for reaction, a 10 hours of catalytic reaction was made. As a result of this, it was confirmed that the catalytic performance was exhibited stably for a long period of time so that a benzene-producing rate of 10 hours later is maintained at 90% of a maximum benzene-producing rate.

Incidentally, as reaction conditions in this experiment, it is disclosed that a pretreatment was carried out before the reaction in such a manner as to combine molybdenum with carbon at 650° C. for 30 minutes, and thereafter the reaction was made at a temperature of 750 CC, a pressure of 3 atmospheres and a methane-space velocity of 2520 mlMFl/g/h.

Based on the experimental conditions disclosed as above, some experiments were conducted in order to confirm an influence of variation of each condition.

1. Influence on Regeneration of Catalytic Activity in Accordance with Difference in the Pretreatment Condition First of all, an influence on regeneration of catalytic activity in accordance with difference in the pretreatment condition was studied. Similar to the experiment disclosed in the above patent publication, 6 wt. %-Mo/HZSM-5 was employed as the catalyst. Pretreatment conditions were set as follow.

(Pretreatment Conditions) The catalyst was increased in temperature to 550° C. in air and then kept at the temperature for 1 hour. Thereafter, the catalyst was increased in temperature to 650° C. while a gas (CH$_4$+9Ar) which contains methane and argon was supplied thereto, and then kept at the temperature for 0.5 hour.

The reaction conditions were set according to the following "Reaction Conditions" based on the experiment disclosed in the above patent publication.

(Reaction Conditions)
Reaction temperature: 750° C.,
Reaction pressure: 0.2 MPaG,
Reaction gas: 100 parts of methane+10 parts of argon+6 parts of hydrogen (methane supplied at a space velocity of 3000 ml/h/g+argon supplied at a space velocity of 300 ml/h/g+hydrogen supplied at a space velocity of 210 ml/h/g).

Change of the supplied gas was set as follows:
a period of time over which the feedstock gas (methane gas) and hydrogen gas were supplied:a period of time over which hydrogen gas alone was supplied (or a period of time over which the supply of the feedstock was suspended)=5 hours:2 hours.

Figure 4:
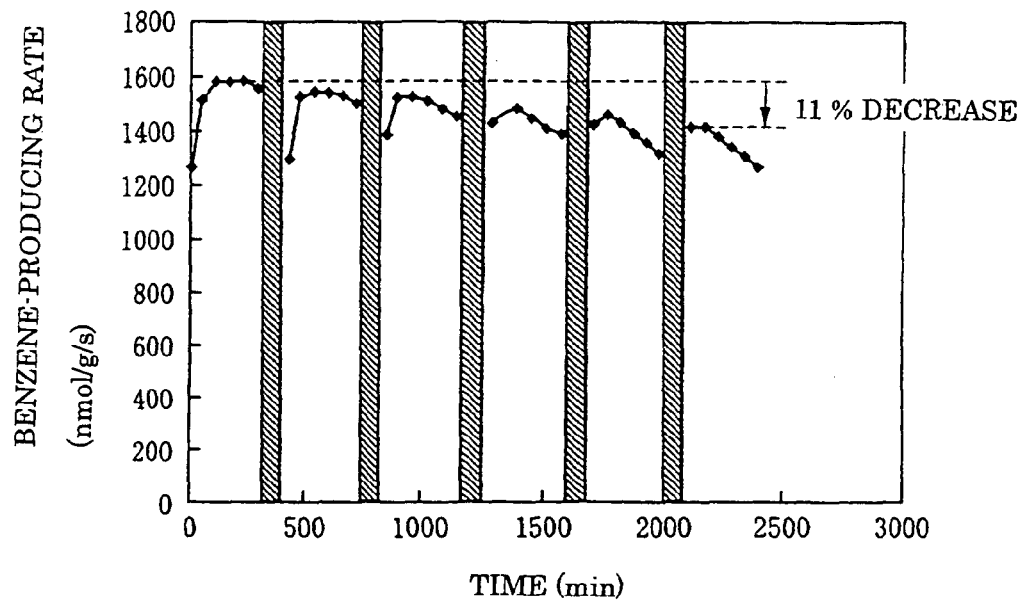
FIG. 4 is a characteristic graph showing a variation with time in a benzene-producing rate, the variation being made by 5 hours of reaction and 2 hours of regeneration of catalytic activity.

FIG. 4 is a characteristic graph showing a variation with time in a benzene-producing rate observed under this reaction conditions. As apparent from this characteristic graph, it was confirmed that: the catalytic activity tended to lower bit by bit in stages from the first reaction tough relatively excellently regenerated; and that a peak value of a benzene-forming ability in the $6^{th}$ reaction, i.e., the reaction after the $5^{th}$ regeneration, was decreased by 11% as compared with that in the first reaction.

Subsequently, an ability to regenerate the catalytic activity was observed upon varying the pretreatment conditions as follow.

(Pretreatment Conditions) The catalyst was increased in temperature to 550° C. in air and then kept at the temperature for 1 hour. Thereafter, the catalyst was increased in temperature to 650° C. while a mixture gas containing methane and hydrogen at a ratio of 1:4 ($CH_4+4H_2$ $CH_4/4H_2$ 75/300 ml/minute) was supplied thereto, and then kept at the temperature for 6.0 hours.

Then, upon making this pretreatment, a cycle in which the reaction was made for 5 hours (by supplying the feedstock gas or methane gas and hydrogen gas) and then the regeneration was made for 2 hours (by supplying hydrogen gas only) was repeated, as same as the experiment relating to FIG. 4.

Figure 5:
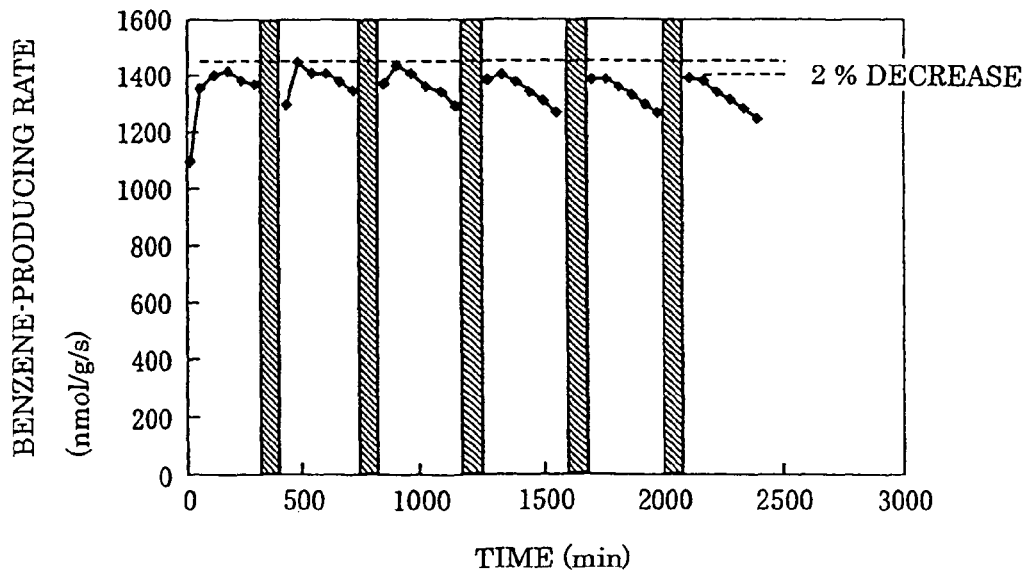
FIG. 5 is a characteristic graph showing a variation with time in a benzene-producing rate, the variation being made by 5 hours of reaction and 2 hours of regeneration of catalytic activity.

FIG. 5 is a characteristic graph showing a variation with time in a benzene-producing rate observed under this reaction conditions. As apparent from this characteristic graph, it was confirmed that: a percentage of decrease in peak value of the catalytic activity after the regeneration was significantly lowered, more specifically a benzene-forming ability in the $6^{th}$ reaction (i.e., the reaction after the $5^{th}$ regeneration) was decreased merely by 2% as compared with that in the first reaction.

From the above-discussed results, it was confirmed that the pretreatment influences the regenerating ability in catalytic activity, and that a suitable pretreatment can extremely suppress decrease in catalytic activity.

2. Influence of the Second Metal on Regeneration of Catalytic Activity

Subsequently, an experiment was conducted by using a catalyst to which Rh (rhodium) serving as the second metal was added in addition to molybdenum, in order to confirm an influence of such a catalyst. The catalyst carrying molybdenum and rhodium in the experiment has a composition discussed as follows.

Zeolite (ZSM-5) carries molybdenum and rhodium in amounts of 6 wt. % and 1.28 wt. %, respectively. The amount of the carried rhodium was a value set based on an effect confirmed by the applicants' experiments, the effect being of using a catalyst having the platinum group metal component such that a mole ratio between the platinum group element (rhodium) and molybdenum was 0.2; 1. The applicants separately apply the point for patent.

The catalyst has such a composition as to be prepared by adding organic hinder, polymeric beads (which was available from Matsumoto Yushi-Seiyaku Co., Ltd. under the trade name of F-80E; and had an average diameter of 90 to 110 μm and a true specific gravity of 0.0025), and a water content to an inorganic component constituted of molybdenum-carrying zeolite (82.5 wt. %); clay (10.5 wt. %); and glass fiber (7 wt. %).

In the use of the catalyst having the above-mentioned composition, an experiment was conducted in order to confirm conditions of the regeneration of catalytic activity. The pretreatment conditions were set pursuant to the experiment relating to FIG. 5. After the pretreatment, a cycle in which the reaction was made for 5 hours (by supplying the feedstock gas or methane gas and hydrogen gas) and then the regeneration was made for 2 hours (by supplying hydrogen gas only) was repeated, as same as the experiment relating to FIG. 5.

Figure 6:
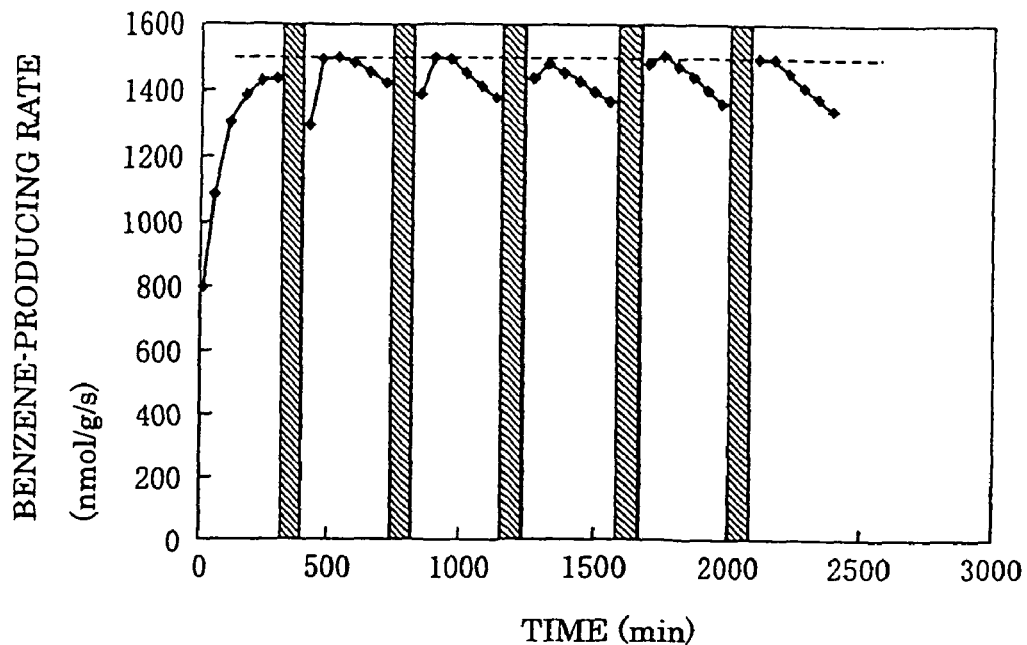
FIG. 6 is a characteristic graph showing a variation with time in a benzene-producing rate, the variation being made by 5 hours of reaction and 2 hours of regeneration of catalytic activity.

FIG. 6 is a characteristic graph showing a variation with time in a benzene-producing rate observed under this reaction conditions. As apparent from this characteristic graph, it is confirmed that the addition of Rh (1.28 wt. %) serving as the second metal allows a 100% regeneration of the catalytic activity in terms of a peak value even in the $6^{th}$ reaction (made upon repeating the cycle of reaction and regeneration for 5 times) without reducing a benzene-forming ability as compared with the first reaction.

Figure 7:
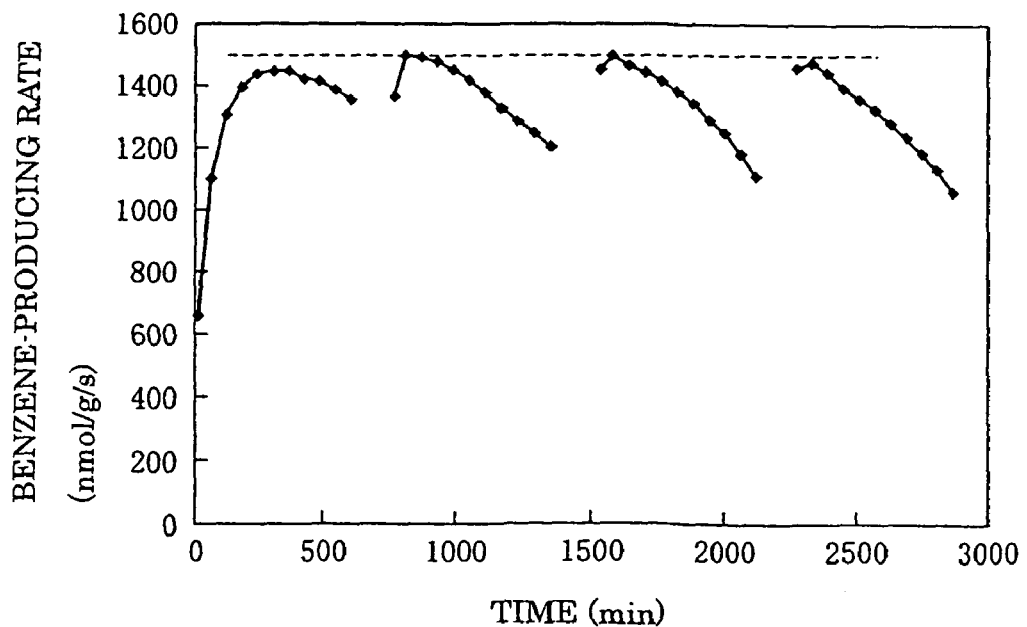
FIG. 7 is a characteristic graph showing a variation with time in a benzene-producing rate, the variation being made by 10 hours of reaction and 2.5 hours of regeneration of catalytic activity.

Further, from a characteristic graph of FIG. 7 showing a variation with time in a benzene-producing rate, it is confirmed that a 100% regeneration of the catalytic activity in terms of a peak value were allowed even in a case a period of time over for the reaction was extended (10 hours of reaction and 2.5 hours of regeneration) in the use of the above-mentioned catalyst.

It is found from these results that the addition of the second metal (Rh) to the catalyst contributes to the regeneration of catalytic activity significantly.

Figure 8:
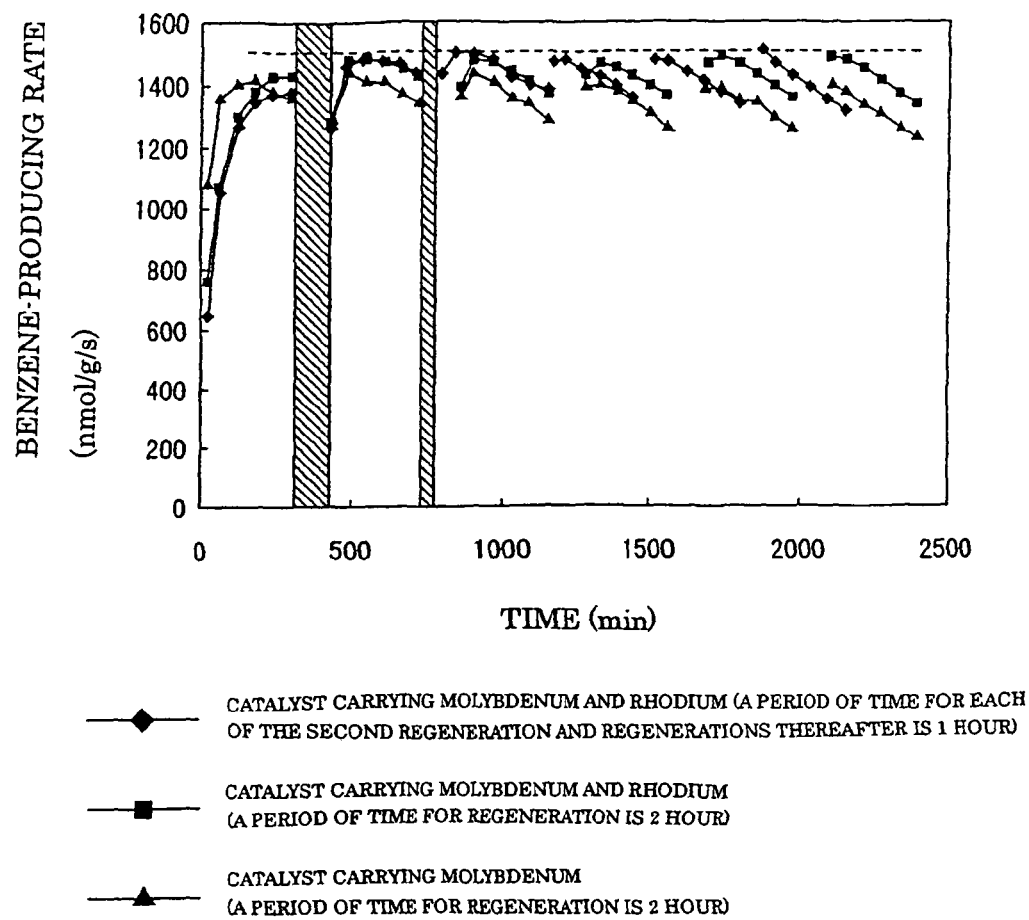
FIG. 8 is a characteristic graph showing a variation with time in a benzene-producing rate, concerning each of various catalysts.

Additionally, concerning a case where a period of time for the first regeneration (made after 5 hours of reaction) was set to 2 hours and where each period of time for regenerations thereafter was set to 1 hour per 5 hours of reaction, it is confirmed that the catalytic activity can be 100% regenerated in terms of a peak value even with the 1 hour of regeneration, as shown in a characteristic graph of FIG. 8 showing a variation with time in a benzene-producing rate. In FIG. 8, black rhombuses represent a plot of a catalyst carrying molybdenum and rhodium (each period of time for the second regeneration and regenerations thereafter was set to 1 hour). Black squares represent a plot of a catalyst carrying molybdenum and rhodium (a period of time for the regeneration was set to 2 hours). Black triangles represent a plot of a catalyst carrying molybdenum (a period of time for the regeneration was set to 2 hours). As apparent from this, it is confirmed that: when a period of time for the first regeneration is suitably set and when the second metal is added to the catalyst, a period of time for the regeneration thereafter can be shortened, thereby forming aromatic hydrocarbons and hydrogen more efficiently.

From the above-discussed results of each of the experiments which are embodiments according to the present invention, it is confirmed that aromatic hydrocarbons and hydrogen can be formed efficiently, for example, with 5 hours of reaction and 2 hours of regeneration; when a period of time for the first regeneration is suitably set (e.g., to 2 hours), each period of time for the regenerations thereafter can be shortened (to 1 hour); and that an efficient reaction for a long period of time (e.g., for 10 hours) is feasible.

Therefore, a period of time for the reaction and that for the regeneration and the like to be applied in each experiment are not limited to those discussed in the above embodiments and can be suitably set in accordance with conditions, circumstances and the like under which the experiment is carried out.

3. Influence of an Amount of Supplied Hydrogen

Then, an influence of variation in an amount of hydrogen gas on the regeneration of catalytic activity was studied by varying an amount of hydrogen gas supplied together with the feedstock gas. The study was conducted by setting an amount of supplied hydrogen within a range determined based on a disclosure of Japanese Patent Provisional Publication No. 2004-269398 that an additive amount of hydrogen is preferably within a range of from 1 to 20%, more preferably has an upper limit of 5% by volume and a lower limit of 15% by volume.

The study was carried out by using the molybdenum and rhodium-carrying catalyst (1.28% Rh-6% Mo ZSM-5) whose effect was confirmed to be excellent by the above experiment. While an amount of supplied hydrogen was varied to 2, 4, 6, 8, 10, and 12%, a cycle of 6 hours reaction (by supplying the feedstock gas or methane gas and hydrogen gas) and 2 hours regeneration (by supplying hydrogen gas only) was repeated under the following pretreatment conditions and reaction conditions with the exception of an amount of hydrogen gas.

(Pretreatment Conditions) The catalyst was increased in temperature to 550° C. in air and then kept at the temperature for 1 hour. Thereafter, the catalyst was increased in temperature to 700° C. while a mixture gas containing methane and hydrogen at a ratio of 1:4 ($CH_4 + 4H_2$ $CH_4/4H_2$ 75/300 ml/minute) was supplied thereto, and then kept at the temperature for 6.0 hours.

(Reaction Conditions)
Reaction temperature: 750° C.,
Reaction pressure: 0.2 MPaG,
Reaction gas: 100 parts of methane+10 parts of argon (methane supplied at a space velocity of 3000 ml/h/g+ argon supplied at a space velocity of 300 ml/h/g).

Figure 9:
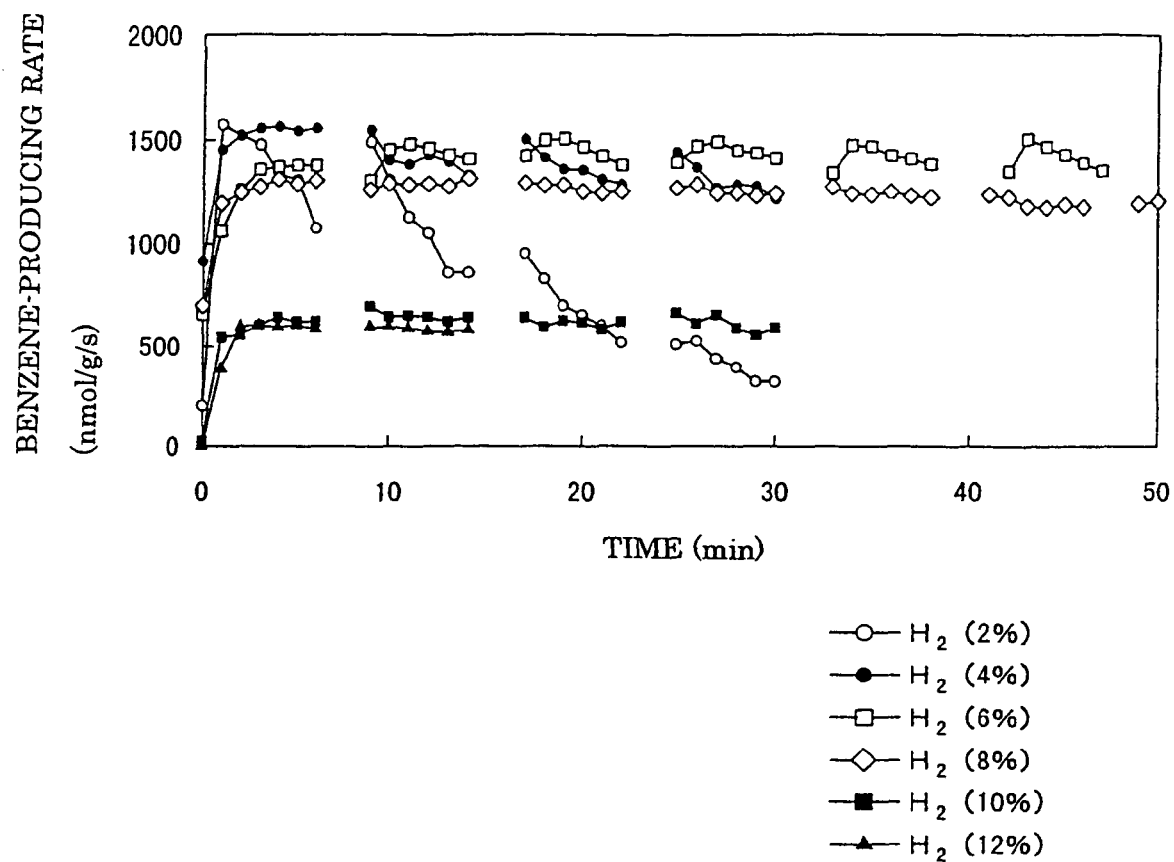
FIG. 9 is a characteristic graph showing a variation with time in a benzene-producing rate, concerning each amount of supplied hydrogen.

FIG. 9 is a characteristic graph showing a variation with time in a benzene-producing rate determined by each of the above-discussed amounts of supplied hydrogen. As apparent from this characteristic graph, concerning a case where an amount of supplied hydrogen is 2% (the case being indicated in FIG. 9 by "$H_2$ (2%)"), it is confirmed that: a benzene-producing rate is significantly decreased with the proceeding of reaction so as to lack stability though a peak value is high in the first reaction; and that the regeneration of catalytic activity is hardly made despite a regenerating process was carried out. Concerning the cases where amounts of supplied hydrogen are 4, 6 and 8% (the cases being indicated in FIG. 9 by "$H_2$ (4%)", "$H_2$ (6%)" and "$H_2$ (8%)", respectively), it is confirmed that a benzene-producing rate is not significantly decreased so as to be stable, and that the regeneration of catalytic activity is sufficiently carried out through the regenerating process. Particularly, the case where an amount of supplied hydrogen is 8% results in an extremely stable benzene-producing rate. Incidentally, in the cases where amounts of hydrogen are 10 and 12% (the cases being indicated in FIG. 9 by "$H_2$ (10%)", "$H_2$ (12%)", respectively), it is confirmed that a benzene-producing rate is low, though the benzene-producing rate is stable and the catalytic activity is maintained by carrying out the regeneration process.

Based on the above-discussed results, it is confirmed that an amount of supplied hydrogen is preferably larger than 2% and smaller than 10%, more preferably within a range of from 4 to 8%, much more preferably 8% in the case of placing importance on the stability.

Although a zeolite formed of ZSM-5 was used in the above-discussed embodiment as a main material for catalyst, an equal effect can be obtained even in other catalysts. For example, the equal effect can be obtained when the main material for catalyst is: aluminosilicate such as molecular sieve 5A, faujasite (of type NaY or NaX) and MCM-22; ALPO-5; VPI-5; FSM-16; MCM-41; or metallo-silicate made of silica and titania.

What is claimed is:

1. A process for producing aromatic hydrocarbons and hydrogen, in which a methane-containing feedstock gas is reformed by being supplied to and being brought into contact with a catalyst under high temperature conditions thereby forming aromatic hydrocarbons and hydrogen, the method comprising the steps of:
    supplying a hydrogen gas together with the methane-containing feedstock gas during supply of the feedstock gas, the hydrogen gas being supplied in an amount of larger than 2% and smaller than 10% by volume of the feedstock gas;
    suspending the supply of the feedstock gas for a certain period of time while continuing to supply the hydrogen gas in the amount of larger than 2% and smaller than 10% by volume of the feedstock gas; and,
    reforming the feedstock gas after being brought into contact with the catalyst under high temperature conditions to produce aromatic hydrocarbons and hydrogen,
    wherein the catalyst includes metallo-silicate carrying molybdenum and rhodium.

2. A process for producing aromatic hydrocarbons and hydrogen, as claimed in claim 1, wherein a pretreatment for a reforming reaction by which aromatic hydrocarbons and hydrogen are formed includes a step of increasing the temperature of the catalyst and then keeping the catalyst at the temperature for a certain period of time while supplying a methane gas thereto.

3. A process for producing aromatic hydrocarbons and hydrogen, as claimed in claim 1, wherein a pretreatment for a reforming reaction by which aromatic hydrocarbons and hydrogen are formed includes a step of increasing the temperature of the catalyst and then keeping the catalyst at the temperature for a certain period of time while supplying a gas containing methane and hydrogen thereto.

4. A process for producing aromatic hydrocarbons and hydrogen, as claimed in claim 3, wherein methane and hydrogen are supplied at a mole ratio of 1:4 during the pretreatment.

5. A process for producing aromatic hydrocarbons and hydrogen, as claimed in claim 3, wherein the pretreatment includes a step of keeping the catalyst at 700° C. for 6 hours while supplying the gas containing methane and hydrogen to the catalyst.

6. A process for producing aromatic hydrocarbons and hydrogen, as claimed in claim 1, wherein the catalyst includes metallo-silicate carrying molybdenum.

7. A process for producing aromatic hydrocarbons and hydrogen, as claimed in claim 1, wherein an amount of the hydrogen gas supplied together with the feedstock gas is within a range of from 4 to 8% by volume of the feedstock gas.

8. A process for producing aromatic hydrocarbons and hydrogen, as claimed in claim 1, wherein an amount of the hydrogen gas supplied together with the feedstock gas is 8% by volume of the feedstock gas.

* * * * *